United States Patent [19]

Brinker et al.

[11] Patent Number: 5,009,897
[45] Date of Patent: Apr. 23, 1991

[54] PHARMACEUTICAL GRANULES AND TABLETS MADE THEREFROM

[75] Inventors: Dale R. Brinker, Antioch; Thomas L. Reiland, Gages Lake, both of Ill.

[73] Assignee: Abbott Laboratories, Abbott Park, Ill.

[21] Appl. No.: 552,377

[22] Filed: Jul. 12, 1990

Related U.S. Application Data

[63] Continuation of Ser. No. 353,809, May 22, 1989, abandoned, which is a continuation-in-part of Ser. No. 211,495, Jun. 24, 1988, abandoned.

[51] Int. Cl.⁵ .......................... A61K 9/16; A61K 9/26; A61K 9/28
[52] U.S. Cl. ...................................... 424/469; 424/80; 424/470; 424/474; 424/494
[58] Field of Search .................. 424/80, 469, 470, 474, 424/494

[56] References Cited

U.S. PATENT DOCUMENTS 4,533,674  8/1985  Schmidt et al. ............. 514/474
4,555,399 11/1989  Hsiao .......................... 424/80

FOREIGN PATENT DOCUMENTS 0196546 10/1986 European Pat. Off. .
2392677 12/1978 France .
WO86/4817  8/1986 PCT Int'l Appl. .
1598458  9/1981 United Kingdom .

Primary Examiner—Thurman K. Page
Attorney, Agent, or Firm—Steven R. Crowley; Steven F. Weinstock

[57] ABSTRACT

A pharmaceutical granule comprising a core of active pharmaceutical agent and a coating of a polymer/microcrystalline cellulose is provided. These granules permit superior tableting of pharmaceutical agents whose physical properties in granule form render them unsuitable for conventional tableting.

11 Claims, 1 Drawing Sheet

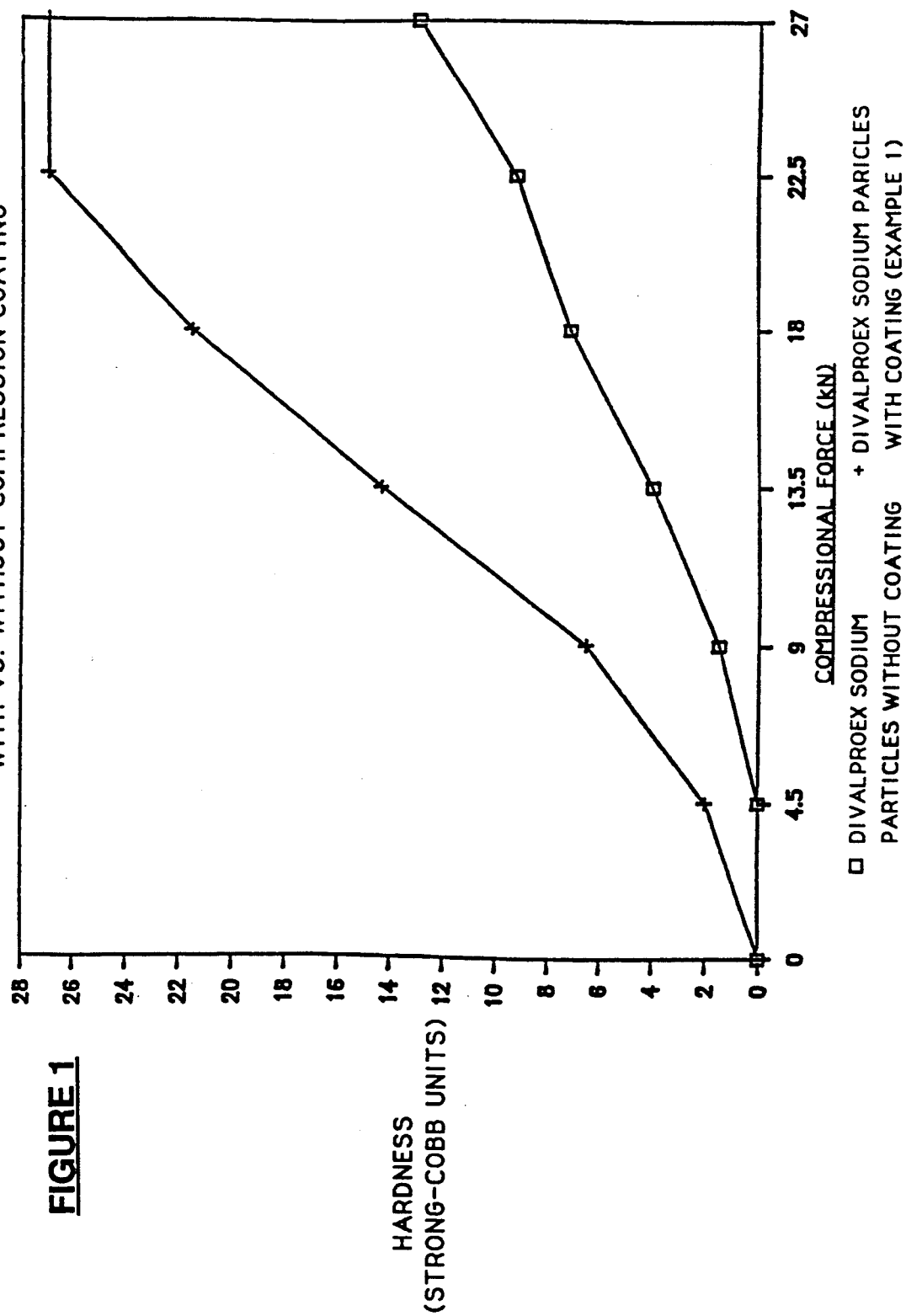

PHARMACEUTICAL GRANULES AND TABLETS MADE THEREFROM

TECHNICAL FIELD

This application is a continuation of application Ser. No. 353,809, filed May 22, 1989, now abandoned, which is a continuation in-part of U.S. patent application Ser. No. 211,495, filed June 24, 1988, now abandoned. This invention relates to pharmaceutical granulations and tablet dosage forms. In particular, it relates to coated pharmaceutical granules and tablets made from such granules.

BACKGROUND ART

In the manufacture of pharmaceutical products, the active pharmaceutical agent is combined with the desired excipients, diluents and other adjuvant materials in a liquid environment and granulated by conventional techniques to produce active drug granules of a size suitable for incorporation in the desired finished product. For tablet products, for example, a granule size of from 10 to 40 mesh may be preferred. In tabletting, the granules are metered into a tablet press and compressed under high pressures to form a cohesive tablet having a certain required degree of physical integrity, surface smoothness, and other physical properties known to the art. The resulting tablet can then be film- or enteric-coated if desired to provide the desired color, flavor, mouthfeel, bioavailability, resistance to abrasion, etc.

Controlled delivery of drugs from pharmaceutical tablets frequently involves the use of coatings to impart acid- or enzyme-resistance, delayed release, and other desirable release properties. A preferred method of employing such coatings is to directly coat a granulation of the desired pharmaceutical active ingredient. Such granules can be almost entirely active drug, or can be built up from nonpareil seeds, or by other techniques readily familiar to those of skill in the pharmaceutical manufacturing arts.

A difficulty is encountered in compressing such coated granules into commercially usable tablet products. Such granules can be formed into relatively soft tablets using low compression forces. However, the compressive forces required to produce a tablet which is sufficiently strong and cohesive to survive the stresses imposed by the subsequent film-coating process and commercial packaging and distribution inevitably result in fracture of the friable coating on a substantial percentage of the granules, resulting in uncontrolled rather than controlled release of the drug.

It has been known in the prior art to incorporate such coated granules into a tablet matrix which further incorporates a material which stabilizes the granules against compressive loads, such as disclosed in European Patent Application 196,546 of Becker. In that application, microcrystalline cellulose is used to form a matrix which effectively distributes compressive loads through the tablet as it is being formed, in effect bypassing the granules as load bearing elements of the tablet during compression.

A problem remains, however, in compressing granules formed from pharmaceutical agents whose physical properties cause the granule to be relatively smooth in surface texture or relatively waxy in overall granule texture. With such agents, such as divalproex sodium, the smooth granule surfaces make it difficult or impossible to achieve acceptable cohesion in tablets formed from the granules, even when very high compression forces are employed. Enteric and other coatings tend to make the surfaces of such smooth granules even smoother, as well as harder, further complicating this problem.

It is an object of this invention to provide a method of tableting drug granules having smooth surfaces which provides acceptable cohesiveness in the resulting tablets.

It is another object of this invention to provide granules which, although made from a material which is difficult to compress into tablets, can be made into tablets having acceptable cohesiveness.

It is a further object of this invention to provide granules and methods which accomplish the foregoing objects while avoiding fracture of any enteric or other coatings on the tablets These and other objects of the invention will be evident from the following disclosure.

Derwent abstract 72723A/41 (GB1598458) discloses a pharmaceutical tablet formulation containing enteric coated granules and microcrystalline cellulose. However, the tablet formulation also contains a polymer or waxy substance to which a granule-protecting activity is ascribed. The abstract in no way attributes the granule-protective action to the content of microcrystalline cellulose. Further, the microcrystalline cellulose is simply admixed in the tablet formulation.

DISCLOSURE OF THE INVENTION

This invention provides pharmaceutical granules and tablets made therefrom. In particular, it provides a granule comprising an active drug, wherein the granule has a compression-enhancing coating comprising a polymer selected from povidone, hydroxypropyl cellulose and hydroxypropyl methylcellulose, and microcrystalline cellulose. Preferably, the coating as applied consists essentially of an ethanol (or any other suitable solvent system) solution of from about 0.5% to about 10% (w/v) povidone and from about 5% to about 25% (w/v) microcrystalline cellulose. In the final, spray-coated granules, i.e., after the ethanol has evaporated, the coating contains from about a 1:15 to about 2:1 by weight povidone:microcrystalline cellulose. Especially preferred as the coating solution is a U.S.P. ethanol solution of 1% povidone K-90 (w/v) and 10% microcrystalline cellulose (w/v). "w/v" as used herein means weight per unit volume of liquid (i.e., grams/liter). While not intending to be limited by theory, it is thought that the polymer material functions as a binder and carrier for the microcrystalline cellulose, while the microcrystalline cellulose itself imparts the excellent compressibility properties to the granules that microcrystalline cellulose is well known for.

The active ingredient in the granules can be any drug accepted for use in pharmaceutical tablet products. Such drugs are well known to those of ordinary skill in the pharmaceutical manufacturing arts. The granules can be made using a single drug or a mixture of drugs, or a mixture of different granules, each containing one or more drugs, can be used. An additional enteric coating, acid-resistant coating, microporous coating, or other coating intended to control the release rate or dissolution rate of the drug granule can be applied to the granule before the compression enhancing coating is applied. Among the materials useful for this purpose are acrylic polymers and copolymers, ethylcellulose, hydroxypropylcellulose, hydroxypropylmethylcellulose, polyvinyl acetate, polyvinyl acetate phthalate, cellulose acetate phthalate, hydroxypropylmethylcellulose phthalate, zein, shellac, acacia, nylon, sugar, anionic acrylic resins, and the like.

The microcrystalline cellulose used in the practice of this invention is an article of commerce, available from a variety of sources, and is a National Formulary material. Its manufacture is described by Battista, *Ind. Eng. Chem.*, 42, 502 (1950) and U.S. Pat. Nos. 2,978,446 and 3,141,875. It is a nonfibrous powder having the particulate form of rigid rods and a bulk density of 18 to 19 pounds per cubic foot. It is practically insoluble in water, but is dispersible therein.

Additional tableting aids, excipients, binders, disintegrants, lubricants, fillers, etc., well known to the pharmaceutical arts can also be employed at minor levels (generally less than 10%, preferably less than 2%) in the practice of this invention. Such inert additives include a variety of stearates, tableting aids, starches, gums, waxes, silicates, polymers and the like. Microcrystalline cellulose can also be employed as a tableting aid apart from its use in the compression-enhancing granule coating of this invention.

If desired, uncoated granules of drug can also be included in the tablet matrix. Just as the coated granules in a given tablet can be made from a single drug or a number of drugs, the uncoated granules optionally incorporated in the tablet matrix can be the same drug or drugs used in the coated granules, or they may be a different drug or mixture of drugs, as dictated by the desires of the formulator.

The compression enhancing particle coating of this invention can be applied by numerous conventional granule coating techniques. For example, the coating can be applied by spraying in a Wurster-type fluidized bed coating apparatus, or by conventional microencapsulation techniques. In a small scale particle coating process, the following operating conditions have been found to be useful: an atomizing air pressure of about 4 atmospheres, an inlet air temperature of about 50° C., a spray rate of about 70 grams/minute for a 3 kg batch of granules, to provide an outlet temperature of from about 28° to about 35° C. At lower temperatures or higher feed rates, overwetting of the particles can occur, while at higher temperatures spray drying of the coating into discrete particles can take place. The resulting coated particles have a core of pharmaceutical active ingredient, and a surface coating of povidone and microcrystalline cellulose. These particles can then be used in any conventional tablet formulation with improved tableting results.

The following Examples illustrate the practice of this invention, without intending to be limitative thereof.

EXAMPLE 1

Nonpareils were coated with an enteric coating liquid made by dissolving 1? % hydroxypropyl methylcellulose phthalate (HP-55), 1% triethyl citrate, and 0.02% dye, blue, FD&C No. 2 in a mixture of 80/20 acetone and 200 proof alcohol, SD 3A. The nonpareils were coated with this coating liquid in a Glatt GPCG-5 Wurster Column Coater. After the coating was applied, 4.5L of a compression-enhancing coating was spray applied to coated batch in the GPCG-5 Particle Coater. The formula for the compression-enhancing coating comprises 1% (w/v) povidone, USP (K-Value 90) and 10% (w/v) microcrystalline cellulose, (Avicel PH 105) in 200 proof alcohol, SD 3A.

The coated (double) nonpareils were then compressed in the following blend:

| Item | | mg/tablet |
|---|---|---|
| 1. | Lactose, Monohydrate, NF, Powder Regular | 40.0 |
| 2. | Cellulose, Microcrystalline, NF (Avicel 101) | 290.0 |
| 3. | Crospovidone, NF | 15.0 |
| 4. | Hydroxypropyl Cellulose, NF | 10.0 |
| 5. | Coated Nonpareils | 840.00 |
| 6. | Acid, Stearic, NF, Fine Powder | 4.0 |
| 7. | Colloidal Silicon Dioxide, NF (Cab-O-Sil) | 1.0 |

The blend was compressed to a tablet weight of 1200 mg.

EXAMPLE 2

249.6 kg of divalproex sodium was blended with 10.4 kg of silica gel in a twin shell blender and milled using a Fitzmill, medium speed knives forward, though a 2A band. This blend was then granulated with 16 liters of alcohol (SD 3A, 200 proof) in a Gral High Intensity Granulator and then dried in an Areomatic Fluid Bed Dryer at an exhaust temperature of 50° C. for 30 minutes. The dried granulation was then sifted through 12 and 24 mesh screens using a Sweco Sifter and the larger than 12 mesh material was milled using a Fitzmill, as above and then resifted.

The 206 kg of 12-24 mesh particles were then coated in a Glatt CPCG-45 Wurster Coating Column using the following coating liquids:

(1) 330 liters of a coating liquid prepared by dispersing 19.8 kg of ethylcellulose (NF, 7 cps), 3.3 kg of triethyl citrate (Citroflex-2), and 19.8 kg of magnesium stearate (NF, impalpable powder) in a mixture of 66 liters of alcohol (SD 3A, 200 proof) and acetone (used to bring the volume of liquid to 330 liters).

(2) 413 liters of a coating liquid prepared by dispersing 41.3 kg of hydroxypropyl methylcellulose phthalate (HP-55), 4.13 kg of triethyl citrate and 826 g of dye (blue, FD&C No. 2) in a mixture of 82.6 liters of alcohol (SD 3A, 200 proof) and acetone (used to bring the volume of liquid to 413 liters).

(3) 310 liter of the Compression Enhancing Coating Liquid prepared by dispersing 3.1 kg of povidone (K-Value 90) and 31 kg of microcrystalline cellulose (Avicel PH 105) in alcohol (SD 3A, 200 proof).

The coating conditions used for each of the coating liquids were as follows:

| Coating Liquid | 1 | 2 | 3 |
|---|---|---|---|
| Inlet Air Temperature (°C.) | 52 | 50 | 52 |
| Relative Humidity (%) | 15 | 15 | 15 |
| Atomization Air Pressure (PSIG) | 65 | 65 | 35 |
| Solution Flow Rate (ml/min/nozzle) | 320 | 280 | 500 |

(NOTE: This unit contains 7 nozzles)

The coated particles are then discharged and sifted through a 10 mesh screen in a Sweco Sifter.

The smaller than 10 mesh particles were then blended with the following items in a twin shell blender and compressed on a Fette 2000 compressing machine.

| Item | mg/tablet |
|---|---|
| 1. Divalproex Sodium Coated Particles | 893.2 |
| 2. Lactose, Monohydrate, NF Powder Reqular | 50.0 |

-continued

| Item |  | mg/tablet |
|---|---|---|
| 3. | Cellulose, Microcrystalline, NF (Avicel PH101) | 291.2 |
| 4. | Crospovidone, NF | 15.0 |
| 5. | Hydroxypropyl Cellulose, NF | 10.0 |
| 6. | Acid, Stearic, NF, Fine Powder | 5.0 |
| 7. | Colloidal Silicon Dioxide, NF (Cab-O-Sil M-5) | 1.2 |

These tablets were then coated in an Accela-Cota (at an exhaust temperature of 35° C., atomization air pressure of 60 psig, liquid spray rate of approximately 700g/min and pan rotating speed of 6 rpm) using 300 ml/kg of tablets with the following coating liquid:

| Item |  | % w/w |
|---|---|---|
| 1. | Water, Purified, USP (Distilled) | 10.0% |
| 2. | Alcohol, SD 3A, 200 Proof | q.s. |
| 3. | Hydroxypropyl Methylcellulose 2910, USP, 6 CPS | 4.0% |
| 4. | Propylene Glycol, USP | 0.8% |
| 5. | Vanillin, NF, Crystals | 0.3% |

EXAMPLE 3

4 kg of erythromycin base was blended with 160 g of microcrystalline cellulose (Avicel PH 101), hydroxypropyl methylcellulose (2910 USP, 15 CPS), and povidone (K-Value 90) in a twin shell blender. This blend was then granulated with 900 ml of distilled water and 50 g of polyethylene glycol 400 in a planetary mixer and extruded through a 0.8 mm band at a speed of 0.4. The extruded material was then spheronized at a speed of 0.7 and then oven dried at 50° C. overnight. The dried granulation was then sifted through 16 and 30 mesh screens using a Sweco Sifter.

The 4 kg of 16-30 mesh particles were then coated in a Glatt CPCG-5 Wurster Coating Column using the following coating liquids:

1. 12 liters of a coating liquid prepared by dispersing 120 g of acetyl tributyl citrate (Citroflex A-4), 1 kg of hydroxypropyl methylcellulose phthalate (HP-50) and 18 g of dye red D&C No. 30 lake in a mixture of 4.8 liters of alcohol (SD 3A, 200 proof) and acetone (used to bring the volume of liquid to 12 liters).
2. 4 liters of the Compression Enhancing Coating Liquid prepared by dispersing 80 g of hydroxypropyl methylcellulose (2910, USP, 15 CPS), 80 g of hydroxypropyl cellulose, 16 g of propylene glycol, and 400 g of microcrystalline cellulose (Avicel PH 101) in alcohol (SD 3A, 200 proof).

The particles were then blended with the following items in a twin shell blender and compressed on a Fette 1000 compressing machine.

| Item |  | mg/tablet |
|---|---|---|
| 1. | Erythromycin Coated Particles | 984.3 |
| 2. | Cellulose, Microcrystalline, NF (Avicel PH 101) | 102.9 |
| 3. | Crospovidone, NF | 102.9 |
| 4. | Magnesium Stearate, NF, Impalpable Powder | 2.5 |
| 5. | Colloidal Silicon Dioxide, NF (Cab-O-Sil M-5) | 2.5 |
| 6. | Talc, USP Powder | 2.5 |
| 7. | Wax, Hydrogenated Vegetable Oil (Sterotex K) | 2.5 |

These tablets were then coated in an Accela-Cota (at an exhaust temperature of 60° C., atomization air pressure of 60 psig, and pan rotating speed of 8 rpm) using 300 ml/kg of tablets with a clear gloss solution.

Compression Profile of Coated Particles

The attached graph (FIG. 1) shows a compressional force versus hardness (measured in Strong-Cobb units) profile for divalproex sodium particles which have been coated with the compression-enhancing coating of Example 1 and divalproex sodium particles which have not been coated with the compression enhancing coating. The data presented in FIG. 1 was obtained using a Strong-Cobb type hardness tester. For the particles with the compression-enhancing coating the hardness data points for 22.5 and 27 kiloNewtons (kN) of compressional force was beyond the capacity of the hardness measuring equipment (>27), but were plotted as hardness of 27.

The graph demonstrates that particles coated with compression-enhancing coating can (1) withstand a greater compressional force and, therefore, are less likely to rupture or fracture, and (2) be made into tablets using a lower compressional force than when a compression-enhancing coating is not used.

Tablets in accordance with this invention having a total weight of about 100 mg, and the coated drug granules contained therein, should have a hardness of at least about 4-5 Strong-Cobb units. Tablets in accordance with this invention having a total weight of about 500-600 mg, and the coated drug granules contained therein, should have a hardness of at least about 10 Strong-Cobb units. Tablets in accordance with this invention having a total weight of about 1000 mg, and the coated drug granules contained therein, should have a hardness of at least about 14 Strong-Cobb units.

The foregoing specification including the examples and formulations are merely illustrative of the invention. Variations and changes which are obvious to one skilled in the art are intended to be within the scope and nature of the invention which are defined in the appended claims.

What is claimed is:

1. A granule for compression into tablets having a hardness sufficient to produce a cohesive tablet that will not fracture during tablet coating, comprising a core of active drug and a surface coating comprising a polymer selected from povidone, hydroxypropyl cellulose and hydroxypropyl methylcellulose and microcrystalline cellulose, the polymer:microcrystalline cellulose ratio being from about 1:15 to about 2:1 by weight.

2. The granule of claim 1 wherein the active drug is divalproex sodium.

3. A tablet having a hardness sufficient to produce a cohesive tablet that will not fracture during tablet coating comprising granules according to claim 1 and tableting excipients.

4. The tablet of claim 3 wherein the active drug is divalproex sodium.

5. The tablet of claim 3 wherein the surface coating comprises 1% (w/v) polyvinylpyrrolidone and 10% (w/v) microcrystalline cellulose.

6. The granule of claim 1 wherein the active drug is erythromycin.

7. The tablet of claim 3 wherein the active drug is erythromycin.

8. A granule for compression into tablets having a hardness sufficient to produce a cohesive tablet that will not fracture during tablet coating, comprising a core of divalproex sodium and a surface coating comprising polyvinylpyrrolidone and microcrystalline cellulose in a ratio of about 1:10 by weight.

9. A tablet having a hardness sufficient to produce a cohesive tablet that will not fracture during tablet coating and comprising drug granules according to claim 8 and tableting excipients.

10. A granule for compression into tablets having a hardness sufficient to produce a cohesive tablet that will not fracture during tablet coating comprising a core of erythromycin and a surface coating comprising hydroxypropyl methylcellulose, hydroxypropyl cellulose and microcrystalline cellulose in a ratio of about 1:1:5 by weight.

11. A tablet having a hardness sufficient to produce a cohesive tablet that will not fracture during tablet coating and comprising drug granules according to claim 10 and tableting excipients.

* * * * *

UNITED STATES PATENT AND TRADEMARK OFFICE
CERTIFICATE OF CORRECTION

PATENT NO. : 5,009,897
DATED : April 23, 1991
INVENTOR(S) : Dale R. Brinker, Thomas L. Reiland It is certified that error appears in the above-identified patent and that said Letters Patent is hereby corrected as shown below:

Column 3, line 57: Replace "1?%" with --10%--.

Signed and Sealed this

Ninth Day of March, 1993

Attest:

STEPHEN G. KUNIN

Attesting Officer

Acting Commissioner of Patents and Trademarks